(12) United States Patent
Wu et al.

(10) Patent No.: US 8,519,958 B2
(45) Date of Patent: Aug. 27, 2013

(54) OPTICAL SENSOR AND OPERATING METHOD THEREOF

(75) Inventors: Chih-Yen Wu, Hsin-Chu (TW); Hsiang-Sheng Liu, Hsin-Chu (TW)

(73) Assignee: Pixart Imaging Inc., Hsin-Chu (TW)

( * ) Notice: Subject to any disclaimer, the term of this patent is extended or adjusted under 35 U.S.C. 154(b) by 864 days.

(21) Appl. No.: 12/027,626

(22) Filed: Feb. 7, 2008

(65) Prior Publication Data
US 2009/0109440 A1   Apr. 30, 2009

(30) Foreign Application Priority Data
Oct. 25, 2007 (TW) .............................. 96140132 A

(51) Int. Cl.
*G09G 5/08* (2006.01)
(52) U.S. Cl.
USPC ............ 345/166; 345/163; 345/169; 345/179
(58) Field of Classification Search
USPC ................. 345/165, 166, 163, 157, 179, 156; 235/472.01, 454; 250/205
See application file for complete search history.

(56) References Cited

U.S. PATENT DOCUMENTS

| | | | |
|---|---|---|---|
| 5,831,254 A * | 11/1998 | Karpen et al. ................ | 235/454 |
| 7,064,311 B2 * | 6/2006 | Jung et al. .................... | 250/205 |
| 2005/0110776 A1 * | 5/2005 | Tan et al. ..................... | 345/179 |
| 2005/0275630 A1 * | 12/2005 | Butterworth et al. ......... | 345/166 |
| 2006/0028442 A1 * | 2/2006 | Bynum et al. ................ | 345/157 |
| 2006/0055666 A1 * | 3/2006 | Chong et al. ................. | 345/156 |
| 2006/0132443 A1 * | 6/2006 | Chien Wu .................... | 345/166 |
| 2006/0255152 A1 * | 11/2006 | Xie et al. ................. | 235/472.01 |

FOREIGN PATENT DOCUMENTS

CN       2643394       *  9/2004

OTHER PUBLICATIONS

English language translation of abstract of CN 2643394 (published Sep. 22, 2004).

* cited by examiner

*Primary Examiner* — Quan-Zhen Wang
*Assistant Examiner* — Troy Dalrymple
(74) *Attorney, Agent, or Firm* — McClure, Qualey & Rodack, LLP

(57) ABSTRACT

The present invention discloses an optical sensor. The optical sensor comprises a sensor for sensing a reflected light, an image capture device coupling with the sensor for reading the reflected light and calculating an average light intensity of the reflected light, a controller coupling with the image capture device for outputting a control signal based on the average light intensity, a driver coupling with the controller for receiving the control signal to output a drive current based on the control signal, and a light source coupling with the driver for receiving the drive current to generate a light.

14 Claims, 4 Drawing Sheets

OPTICAL SENSOR AND OPERATING METHOD THEREOF

RELATED APPLICATIONS

This application claims priority to Taiwan Application Serial Number 96140132, filed Oct. 25, 2007, which is herein incorporated by reference.

FIELD OF THE INVENTION

The present invention relates to a sensor, and in particular, to an optical sensor and operating method thereof.

BACKGROUND OF THE INVENTION

An optical mouse is an advanced computer pointing device that uses a light-emitting diode (LED), an optical sensor, and digital signal processing (DSP) in place of the traditional mouse ball and electromechanical transducer. The optical mouse detects movements by sensing changes in reflected light, rather than by interpreting the motion of a rolling sphere.

The optical mouse takes microscopic snapshots of the working surface at a rate of more than 1,000 images per second. Digital signal processing detects changes between one frame and the next and translates these changes into movement on the two axes using an optical flow estimation algorithm.

However, some surfaces do not allow the sensor and DSP to function properly because the intensity of the reflected light is too low and cannot be detected. In this case, the frame rate of the optical sensor is adjusted to increase the exposure time to compensate for the low intensity reflected light. However, such compensating methods reduce the optical mouse efficiency.

Therefore, what is needed is a system and method to compensate the low intensity reflected light while meeting the optical mouse efficiency.

SUMMARY OF THE INVENTION

The main purpose of the present invention is to provide an optical sensor and operation method thereof. According to an embodiment, the optical mouse efficiency that can vary the lightness of the light source based on the reflected surface to improve the reflected light.

In accordance with the foregoing purpose, the present invention discloses an optical sensor. The optical sensor comprises a sensor, an image capture device, a controller and a light source. The sensor senses the reflected light. The image capture device is coupled to the sensor. The image capture device reads the reflected light and calculates the average light intensity of the reflected light. The controller is coupled to the image capture device and outputs a control signal based on the average light intensity. The driver coupled to the controller outputs a drive current based on the control signal received from the controller. The light source coupled to the driver receives the drive current to generate a light.

In accordance with another embodiment, the present invention discloses a method to adjust the light source in real time based on sensed light intensity. The light source can generate a first light signal. A surface reflects the first light signal thereby generating a second light signal. The method comprises the following steps. First, the second light signal is sensed in a predetermined time period. Next, the second light signal is read to calculate an average light intensity of the second light signal. Then, the average light intensity is compared with a predetermined value. Finally, the second light signal is adjusted to the third light signal when the average light intensity is different from the predetermined value.

Accordingly, it is not necessary to adjust the frame rate of the optical sensor to compensate the small reflected light. Therefore, the optical mouse efficiency does not be affected.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

Figure 1:
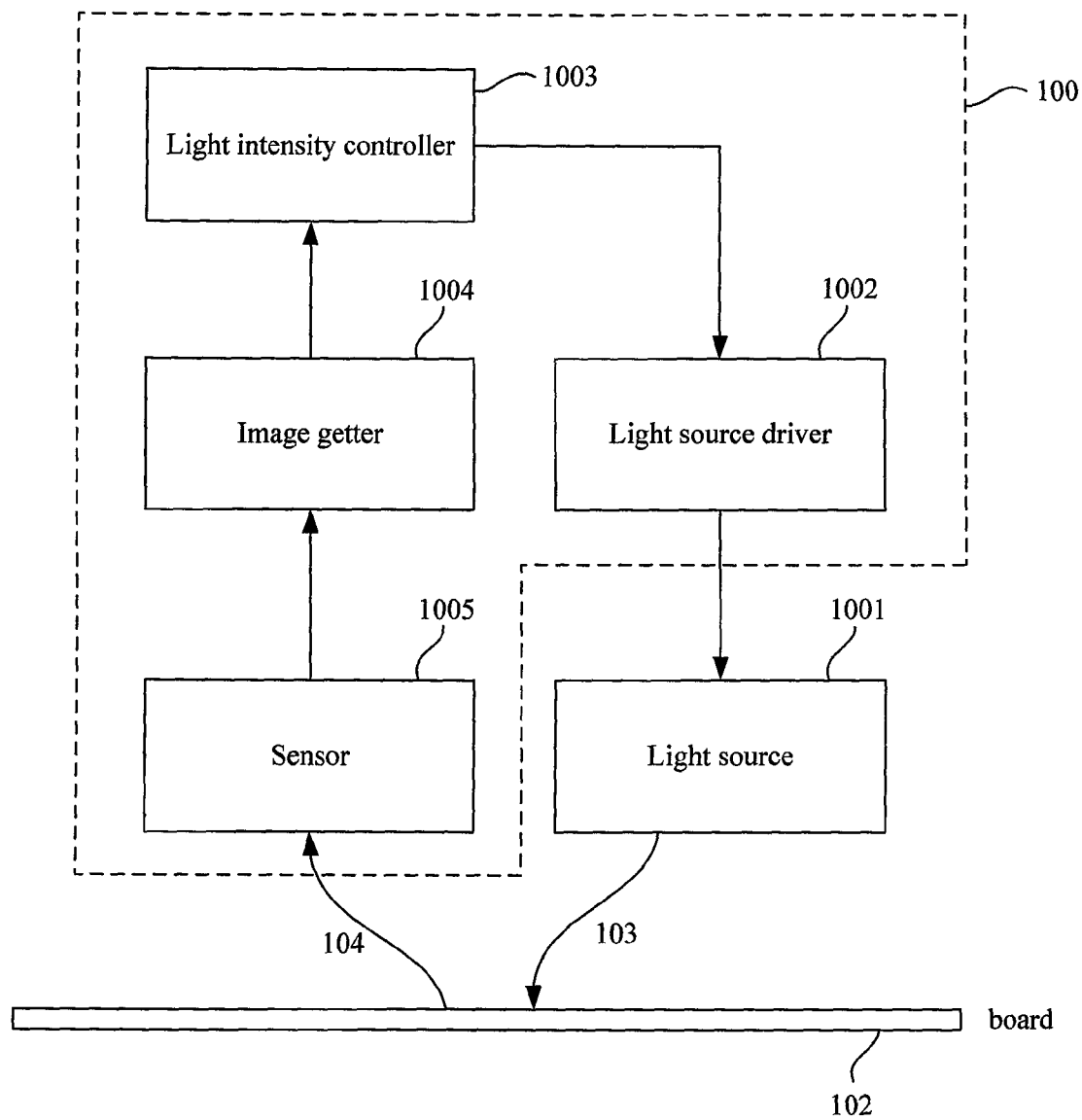
FIG. 1 illustrates a schematic diagram of an optical sensor that can adjust the light source intensity based on the surface condition.

FIG. 1 illustrates a schematic diagram of an optical sensor that can adjust the light source intensity based on the surface condition according to an embodiment of the present invention. The optical sensor 100 comprises a light source 1001, a light source driver 1002, a light intensity controller 1003, an image capture device 1004 and a sensor 1005. In an embodiment, laser diodes or light emitting diodes can serve as the light source 1001.

In an embodiment, the optical sensor is disposed in an optical mouse.

The light source 1001 generates a light signal 103 when the optical mouse moves on the board 102. The light signal 103 illuminates the board 102 to enable the detection of any movement of the mouse. The board 102 reflects the light signal 103. After the sensor 1005 detects the reflected light signal 104, the reflected light signal 104 moves from the sensor 1005 to the image capture device 1004. The image capture device 1004 can analyze the reflected light signal 104 to decide if the light intensity from the light source 1001 has reached the predetermined value and transfers the decision to the light intensity controller 1003. Then, the light intensity controller 1003 can control the light source driver 1002 to modify the drive current sent to the light source 1001 based on the decision.

In other words, the light intensity of the light source 1001 is adjustable based on the board 102 condition. For example, if the board 102 has a dark surface so that the reflected light signal 104 is weak, the image capture device 1004 can determine the intensity of the reflected light signal 104 does not reach a predetermined value and transfer the determined result to the light intensity controller 1003. Then, the light intensity controller 1003 can instruct the light source driver 1002 to raise the drive current sent to the light source 1001 to increase the light signal 103. Therefore, the intensity of the reflected light signal 104 is also increased. In other words, the low reflecting light rate of the dark surface is compensated by increasing the light intensity of the light signal 103. According to the present invention, it is not necessary for the optical sensor 100 to change its frame rate to get the same exposure time. Therefore, the performance of the optical sensor 100 is kept.

On the other hand, if the board 102 has a smooth surface so that the reflected light signal 104 is too strong, the image capture device 1004 can decide the intensity of the reflected light signal 104 is over a predetermined value and transfers the decided result to the light intensity controller 1003. Then, the light intensity controller 1003 can instruct the light source driver 1002 to reduce the drive current sent to the light source 1001 to weaken the light signal 103. Reducing the drive current weakens the intensity of the reflected light signal 104 and reduces the power consumption of the light source 1001. In this embodiment, the light source driver 1002 changes the drive current sent to the light source 1001. However, in other embodiments, the light source driver 1002 modifies the drive current sent to the light source 1001.

Figure 2:
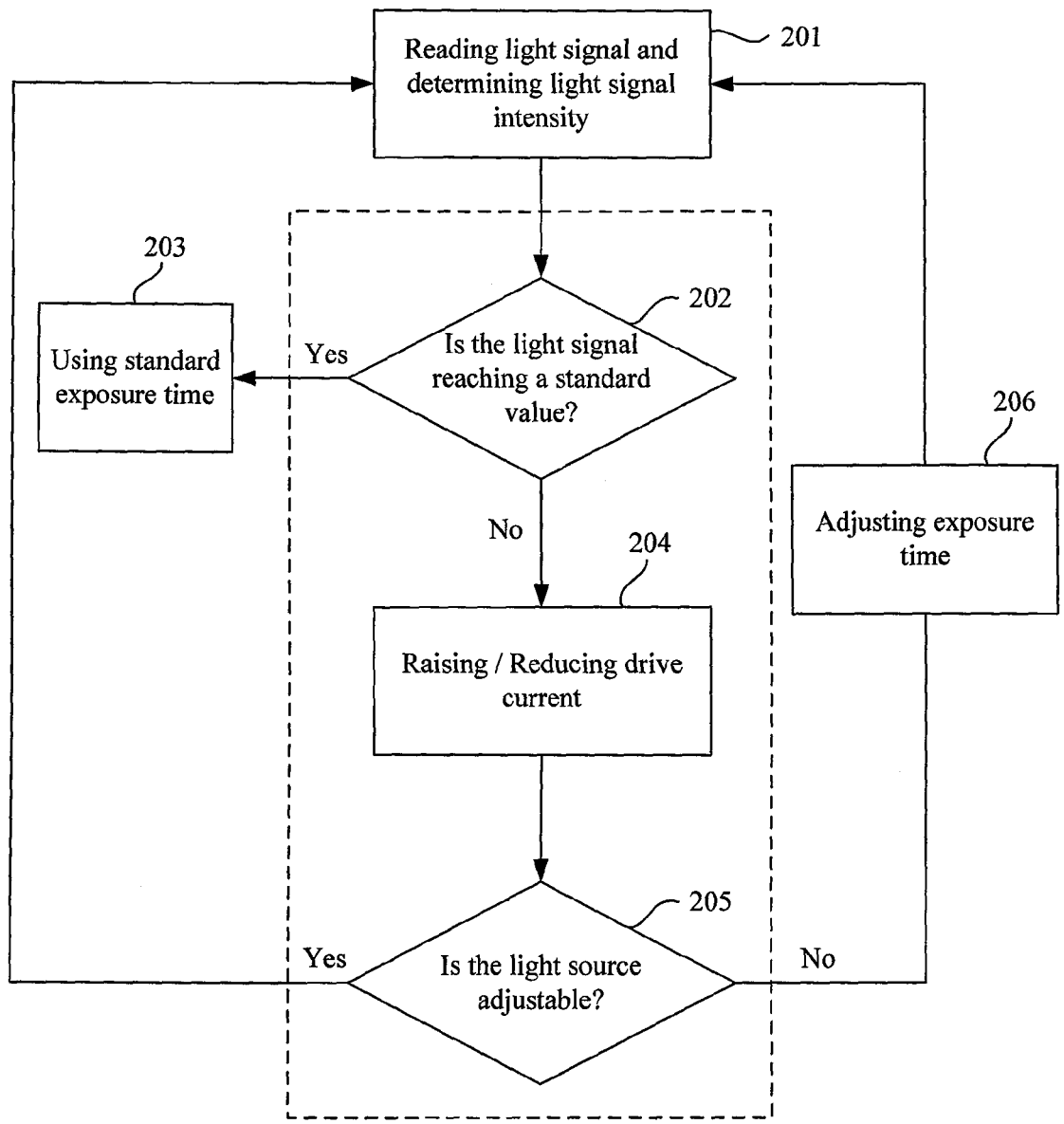
FIG. 2 illustrates a flow chart for adjusting the light source intensity based on the surface condition.

FIG. 2 illustrates a flow chart for adjusting the light source intensity based on the surface condition. Please refer to FIG. 1 and FIG. 2. In step 201, the image capture device 1004 analyzes the reflected light signal 104 from the sensor 1005 to determine the value of the light intensity of the reflected light signal 104. Next, in step 202, the value of the light intensity of the reflected light signal 104 is compared with a predetermined light intensity standard to decide whether or not the value reaches the standard. When the light intensity reaches the standard, step 203 is performed. In step 203, the sensor 1005 uses standard exposure time to sense the value of the light intensity. When the light intensity does not reach the standard, step 204 is performed. In step 204, the light intensity controller 1003 instructs the light source driver 1002 to adjust the drive current sent to the light source 1001. Then, a secure step 205 ensures the adjusted drive current is in an acceptable drive current range of the light source 1001. If the adjusted drive current located in the acceptable drive current range, the adjusted drive current will be sent to the light source 1001 to adjust the output light signal 103 and the step 201 is performed again. On the other hand, if the adjusted drive current is over the acceptable drive current range, the adjusted drive current is not sent to the light source 1001 and the step 206 is performed. In step 206, the frame rate of the sensor 1005 is adjusted to raise or reduce the exposure time.

Figure 4:
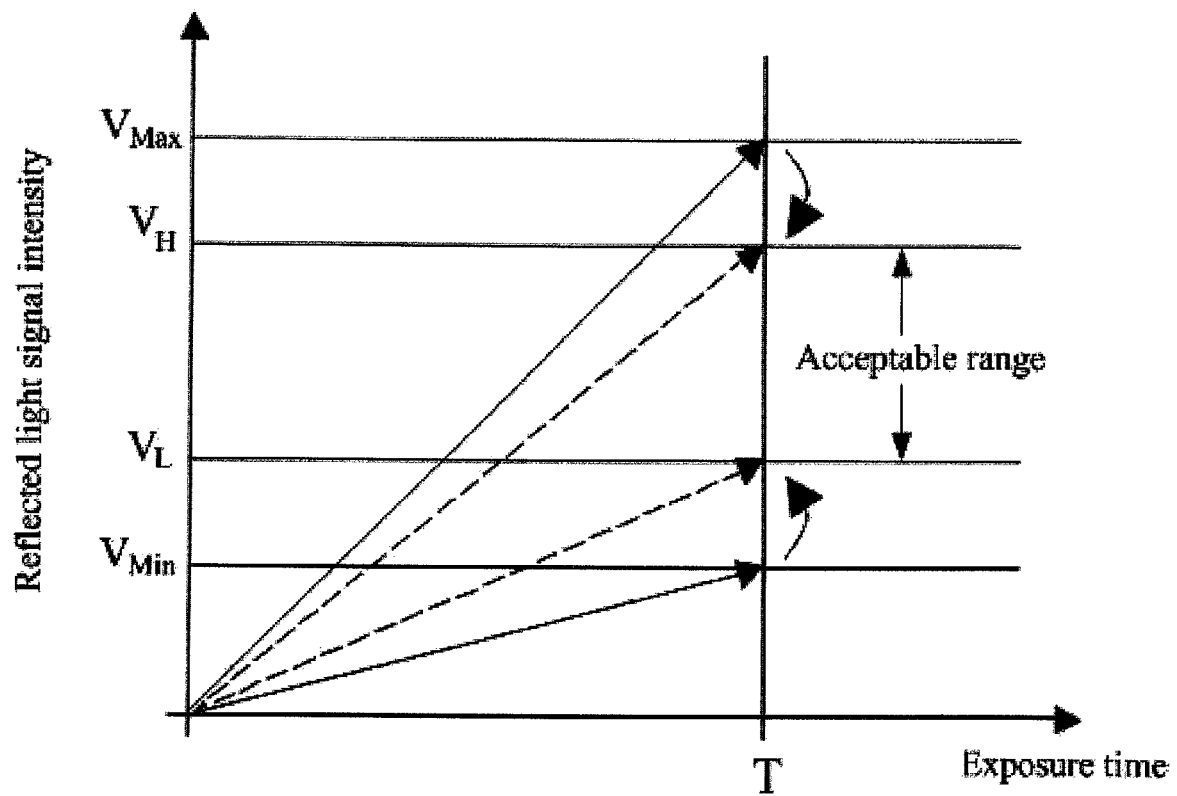
FIG. 4 illustrates an acceptable range of reflected light intensity under a predetermined exposure time.

On the other hand, a reflected light signal range that permits varying the light source is set to prevent the light source 1001 being adjusted too often as shown in the FIG. 4. That is that the drive current is adjusted only when the reflected light signal 104 is over the set reflected light signal range.

According to the FIG. 4, the exposure time is T. The reflected light signal range that the light source 1001 illuminates the same intensity light signal 103 is located between $V_H$ and $V_L$. The maximum value and the minimum value of the reflected light signal are $V_{max}$ and $V_{min}$ respectively. In other words, when the change of the reflected light signal is located in the range of between $V_H$ and $V_L$, the light source driver 1002 does not adjust the drive current of the light source 1001. When the reflected light signal is higher than $V_H$, the light source driver 1002 reduces the drive current to reduce the reflected light signal 104 of the light source 1001 to $V_H$. When the reflected light signal is lower than $V_L$, the light source driver 1002 increases the drive current to increase the reflected light signal 104 of the light source 1001 to $V_L$.

Figure 3:
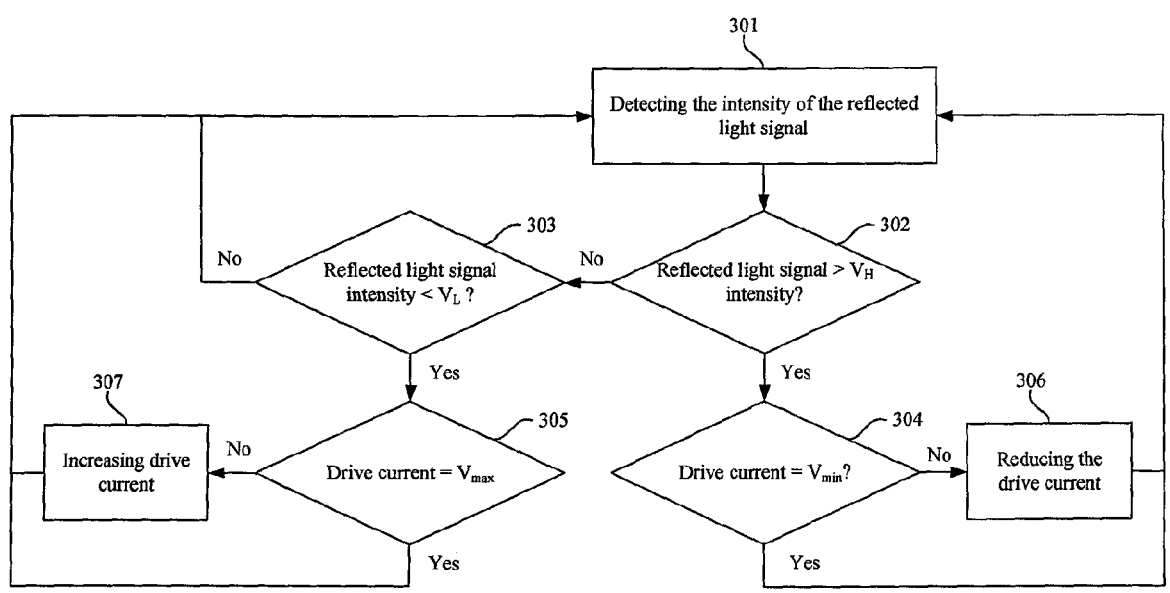
FIG. 3 illustrates a flow chart for adjusting drive current of the light source based on the surface condition.

FIG. 3 illustrates a flow chart for adjusting drive current of the light source based on the surface conditions and the reflected light signal range. In step 301, the intensity of the reflected light signal 104 is detected by the sensor 1005. In step 302, the intensity of the reflected light signal is compared with the $V_H$ to determine whether or not the light signal intensity is larger than $V_H$. When the intensity of the reflected light signal 104 is less than $V_H$, the step 303 is performed. In step 303, the intensity of the reflected light signal 104 is compared with the $V_L$ to determine whether or not the light signal intensity is less than $V_L$. When the intensity of the reflected light signal 104 is larger than $V_L$ and less than $V_H$, the intensity of the reflected light signal 104 is located in the range. Therefore, the drive current for the light source 1001 remains the same. When the intensity of the reflected light signal 104 is higher than $V_H$, the step 304 is performed. In step 304, the value of the drive current is compared with the $V_{min}$ to determine whether or not the current value is equal to the $V_{min}$. When the current value is not equal to the $V_{min}$, the step 306 is performed to reduce the drive current to reduce the reflected light signal 104 to $V_H$. On the other hand, when the current value is less or equal to the $V_{min}$, the reflected light signal 104 can not be further reduced by reducing the drive current. Therefore, the step 301 is performed again.

When the intensity of the reflected light signal 104 is lower than $V_L$, the step 305 is performed. In step 305, the value of the drive current is compared with the $V_{max}$ to determine whether or not the current value is equal to the $V_{max}$. When the current value is not equal to the $V_{max}$, the step 307 is performed to increase the drive current to increase the reflected light signal 104 to $V_L$. On the other hand, when the current value is over or equal to the $V_{max}$, the reflected light signal 104 can not be further increased by increasing the drive current. Therefore, the step 301 is performed again.

It is noticed that the intensity of the reflected light signal 104 is always changed to $V_H$ or $V_L$ in the above embodiment. However, in other embodiments, the intensity of the reflected light signal 104 can be changed to the location between $V_H$ and $V_L$.

While the preferred embodiment of the invention has been illustrated and described, it will be appreciated that various changes can be made therein without departing from the spirit and scope of the invention.

What is claimed is:

1. An optical sensor, comprising:
   a sensor for sensing a reflected light;
   an image capture device coupling with the sensor for reading the reflected light and calculating an average light intensity of the reflected light;
   a controller coupling with the image capture device for outputting a control signal based on the average light intensity of the reflected light;
   a driver coupling with the controller for receiving the control signal to output a variable drive current based on the control signal, wherein the control signal can vary the drive current to a first drive current when a light intensity of the reflected light is not located between a first light intensity and a second light intensity, wherein the first drive current can vary a light intensity of the first light to make a light intensity of the reflected light located between a first light intensity and a second light intensity, wherein the first light intensity is larger than the second light intensity; and
   a light source coupling with the driver for receiving the variable drive current to generate a light being variable in intensity according to the variable drive current, wherein the reflected light read by the image capture device is only from the light source when the control signal is outputted;
   wherein the light is reflected by a surface to be the reflected light, and the driver generates the variable driver current to compensate a change in the reflected light to make the image capture device reads the reflected light in a single, predetermined frame rate, wherein the optical sensor efficiency does not be affected, and the single, predetermined frame rate is adjusted when the variable driver current reaches a limit that the driver can generate.

2. The optical sensor as claimed in claim 1, wherein the light source is a laser diode or a light emitting diode.

3. The optical sensor as claimed in claim 1, wherein the control signal can vary the duty cycle of the drive current to a first duty cycle when a light intensity of the reflected light is not located between a first light intensity and a second light intensity, wherein the drive current with the first duty cycle can vary a light intensity of the first light to make a light intensity of the reflected light located between a first light intensity and a second light intensity.

4. A method to adjust a light source based on sensed light intensity of an optical sensor, wherein a drive current generated by a driver drives the light source to generate a first light signal, the first light signal is reflected by a surface to generate a second light signal, the method comprising:
   detecting the second light signal in a single, predetermined frame rate, wherein the second light signal is only from the light source;
   reading the second light signal to calculate an average light intensity of the second light signal;
   determining whether or not the average light intensity is located between a first light intensity and a second light intensity, wherein the first light intensity is larger than the second light intensity; and
   varying the drive current to adjust the first light signal to a third light signal when the average light intensity is not located between the first light intensity and the second light intensity, wherein the varied driver current compensates a change in the second light signal to make the optical sensor operate in the single, predetermined frame rate, and wherein when the varied driver current reaches a limit that the driver can generate, the single, predetermined frame rate is adjusted.

5. The method as claimed in claim 4, wherein the light source is a laser diode or a light emitting diode.

6. The method as claimed in claim 4, further comprising:
   determining whether or not the light source can generate the third light signal; and
   varying the predetermined time period when the light source can not generate the third light signal.

7. The method as claimed in claim 4, further comprising:
   keeping the first light signal when the average light intensity of the second light signal is located between the first light intensity and the second light intensity.

8. The method as claimed in claim 4, wherein the intensity of the first light signal is larger than the intensity of the third light signal when the average light intensity of the second light signal is larger than the first light intensity.

9. The method as claimed in claim 4, wherein the intensity of the first light signal is less than the intensity of the third light signal when the average light intensity of the second light signal is less than the second light intensity.

10. A method to adjust a light source based on sensed light intensity of an optical sensor, wherein a drive current generated by a driver drives the light source to generate a first light signal, the first light signal is reflected by a surface to generate a second light signal, the method comprising:
    setting a light intensity range limited by a first light intensity and a second light intensity, wherein the first light intensity is larger than the second light intensity;
    detecting the second light signal in a single, predetermined frame rate, wherein the second light signal is only from the light source;
    reading the second light signal to calculate an average light intensity of the second light signal;
    comparing the average light intensity with the light intensity range; and
    varying the drive current to adjust the second light signal to a third light signal when the average light intensity is not located in the light intensity range, wherein the varied driver current compensates a change in the second light signal to make the optical sensor operate in the single, predetermined frame rate, and wherein when the varied driver current reaches a limit that the driver can generate, the single, predetermined frame rate is adjusted.

11. The method as claimed in claim 10, wherein the light source is a laser diode or a light emitting diode.

12. The method as claimed in claim 10, further comprising:
    determining whether or not the light source can generate the third light signal; and
    varying the predetermined time period when the light source can not generate the third light signal.

13. The method as claimed in claim 10, further comprising:
    keeping the first light signal when the average light intensity of the second light signal is located in the light intensity range.

14. The method as claimed in claim 10, wherein the third light signal is reflected by the surface to generate a fourth light signal, and the average light intensity of the fourth light signal is located in the light intensity range.

* * * * *